United States Patent
Kim et al.

(10) Patent No.: US 6,537,551 B2
(45) Date of Patent: Mar. 25, 2003

(54) ANTI-TUMOR AGENT COMPRISING SALMOSIN AS AN ACTIVE INGREDIENT

(75) Inventors: Doo-Sik Kim, 84-3, Yeonhee-dong, Seodaemun-gu, Seoul 120-110 (KR); Kwang Hoe Chung, Sungnam (KR); In-Cheol Kang, Suwon (KR)

(73) Assignee: Doo-Sik Kim, Seoul (KR)

( * ) Notice: Subject to any disclaimer, the term of this patent is extended or adjusted under 35 U.S.C. 154(b) by 0 days.

(21) Appl. No.: 09/776,268

(22) Filed: Feb. 2, 2001

(65) Prior Publication Data

US 2001/0023242 A1 Sep. 20, 2001

Related U.S. Application Data

(62) Division of application No. 09/335,088, filed on Jun. 17, 1999, now abandoned.

(30) Foreign Application Priority Data

Jun. 23, 1998 (KR) .............................. 98-23778
Jun. 4, 1999 (KR) .............................. 99-20579

(51) Int. Cl.$^7$ .............................................. A61K 39/00
(52) U.S. Cl. .................................................. 424/185.1
(58) Field of Search ........................... 530/324; 514/12; 424/185.1

(56) References Cited

PUBLICATIONS

In–Cheol Kang et al., Purification and Molecular Cloning of a Platelet Aggregation Inhibitor from the Snake (*Agkistrodon halys brevicaudus*) Venom, Thrombosis Research, 91:65–73 (1998).
Dongsu Park et al., Cloning and Characterization of Novel Disintegrins from *Agkistrodon Halys* Venom, Mol, Cells., 8(5):578–584 (1998).
Burnhilde Felding–Habermann et al., Involvement of Integrin αV Gene Expression in Human Melanoma Tumorigenicity, J. Clin. Invest., 89:2018–2022 (1992).
Renata Pasqualini et al., A Polymeric Form of Fibronectin has Antimetastatic Effects Against Multiple Tumor Types, Nature Medicine, 2(11):1197–1203 (1996).
Stefan Niewiarowski et al., Disintegrins and Other Naturally Occuring Antagonists of Platelet Fibrinogen Receptors, Seminars in Hematology, 31(4):289–300 (1994).

Mohit Trikha et al., Contortrostatin, a Snake Venom Disintegrin, Inhibits $\beta_1$ Integrin–mediated Human Metastatic Melanoma Cell Adhesion and Blocks Experimental Metastasis, Cancer Research 54(15):4993–4998 (1994).
Martin Friedlander et al., Definition of Two Angiogenic Pathways by District $\alpha_v$ Integrins, Science, 270(1):1500–1502 (1995).
Mal Nguyen et al., A Role for Sialys Lewis–X/A Glycoconjugates in Capillary Morphogenesis, Nature, 365(16):267–269.
Peter C. Brook et al., Integrin $\alpha_v\beta_3$ Antagonists Promote Tumor Regression by Inducing Apoptosis of Angiogenic Blood Vessels, Cell, 79(3):1157–1164 (1994).
Richard O. Hynes, Integrins: A Family of Cell Surface Receptors, Cell 48(27):549–554 (1987).
Hannu Larjava et al., Novel Function for $\beta_1$ Integrin in Keratinocyte Cell–Cell Interaction, J. Cell Biol., 110:803–815 (1990).
Erkki Ruoslahti, How Cancer Spreads, *Scientific American*, 73–77, Sep. (1996).
Steven M. Albelda et al., Integrin Distribution in Malignant Melonoma: Association of the $\beta_3$ Subunit with Tumor Progression, Cancer Research 50(15):6757–6764 (1990).
Filippo G. Giancotti et al., Elevated Level of the $\alpha_5\beta_a$ Fibronectin Receptor Suppress the Transformed Phenotype of Chinese Hamster Ovary Cells, Cell, 60(9):849–859 (1990).
Judah Folkman, et al., "Blood Vessel Formation: What is its Molecular Basis?", Cell, 87(77):1153–1155 (1996) 3 pp.

*Primary Examiner*—Patrick J. Nolan
*Assistant Examiner*—Amy Decloux
(74) *Attorney, Agent, or Firm*—Darby & Darby

(57) ABSTRACT

The present invention relates to an anti-tumor agent comprising Salmosin which is a novel disintegrin containing Arg-Gly-Asp (RGD) sequence and derived from venom of Korean snake, *Agkistrodon halys brevicaudus,* as an active ingredient. Salmosin is a disintegrin which blocks the function of αvβ3 integrin and strongly inhibits tumor angiogenesis, tumor metastasis as well as growth of solid tumor. Salmosin does not exhibit cytotoxicity within an effective dose range where tumor growth is efficiently suppressed without any untoward effect on preexisting blood vessels and normal angiogenesis. Accordingly, Salmosin can be applied for the development of potent anti-tumor drugs which are effective for various types of cancers.

2 Claims, 8 Drawing Sheets

- PBS -

<br>
- Salmosin -

FIG. 7B

<br>
- PBS -

<br>
- Salmosin -

FIG. 8

SEQUENCE LISTING

<160> NUMBER OF SEQ ID NOS: 7

<210> SEQ ID NO 1
<211> LENGTH: 73
<212> TYPE: PRT
<213> ORGANISM: Agkistrodon halys brevicaudus

<400> SEQUENCE: 1

Glu Ala Gly Glu Glu Cys Asp Cys Gly Ser Pro Gly Asn Pro Cys Cys
1               5                   10                  15

Asp Ala Ala Thr Cys Lys Leu Arg Gln Gly Ala Gln Cys Ala Glu Gly

-continued

```
                    20                  25                  30
Leu Cys Cys Asp Gln Cys Arg Phe Met Lys Glu Gly Thr Ile Cys Arg
             35                  40                  45
Arg Ala Thr Arg Asp Asp Leu Asp Asp Tyr Cys Asn Gly Ile Ser Ala
     50                  55                  60
Gly Cys Pro Arg Asn Pro Phe His Ala
 65                  70
```

<210> SEQ ID NO 2
<211> LENGTH: 20
<212> TYPE: DNA
<213> ORGANISM: Artificial Sequence
<220> FEATURE:
<223> OTHER INFORMATION: single stranded oligonucleotide as 5' primer
<220> FEATURE:
<221> NAME/KEY: misc_feature
<222> LOCATION: (1)..(20)
<223> OTHER INFORMATION: n can be any nucleotide

<400> SEQUENCE: 2
ggngargart gygaytgygg                                              20

<210> SEQ ID NO 3
<211> LENGTH: 222
<212> TYPE: DNA
<213> ORGANISM: Agkistrodon halys brevicaudus

<400> SEQUENCE: 3
gaggccggag aagaatgtga ctgtggctct cctggaaatc cgtgctgtga tgctgcaacc    60
tgtaaactga acaaggagc acagtgtgca gaaggactgt gctgtgacca gtgcagattt   120
atgaaagaag gaacaatatg ccggagagca acgcgtgatg acctggatga ttactgcaat   180
ggcatatctg ctggctgtcc cagaaatccc ttccatgcct aa                    222

<210> SEQ ID NO 4
<211> LENGTH: 6
<212> TYPE: PRT
<213> ORGANISM: Artificial Sequence
<220> FEATURE:
<223> OTHER INFORMATION: synthetic RGD peptide

<400> SEQUENCE: 4

Gly Arg Gly Asp Ser Pro
 1               5

<210> SEQ ID NO 5
<211> LENGTH: 6
<212> TYPE: PRT
<213> ORGANISM: Agkistrodon halys brevicaudus

<400> SEQUENCE: 5

Glu Glu Cys Asp Cys Gly
 1               5

<210> SEQ ID NO 6
<211> LENGTH: 6
<212> TYPE: PRT
<213> ORGANISM: Artificial Sequence
<220> FEATURE:
<223> OTHER INFORMATION: N-terminal sequence of recombinant Salmosin

<400> SEQUENCE: 6

Glu Ala Gly Glu Glu Cys
 1               5

```
<210> SEQ ID NO 7
<211> LENGTH: 6
<212> TYPE: PRT
<213> ORGANISM: Artificial Sequence
<220> FEATURE:
<223> OTHER INFORMATION: synthetic RGE peptide

<400> SEQUENCE: 7

Gly Arg Gly Glu Thr Pro
1               5
```

ANTI-TUMOR AGENT COMPRISING SALMOSIN AS AN ACTIVE INGREDIENT

This is a division of application Ser. No. 09/335,088, filed Jun. 17, 1999 now abandoned. Each of these prior applications is hereby incorporated herein by reference, in its entirety.

FIELD OF THE INVENTION

The present invention relates to an anti-tumor agent comprising a disintegrin derived from snake venom, more specifically, to an anti-tumor agent comprising Salmosin which is a novel disintegrin containing Arg-Gly-Asp (RGD) sequence and derived from venom of Korean snake, *Agkistrodon halys brevicaudus,* as an active ingredient.

BACKGROUND OF THE INVENTION

Tumor invasion and metastasis are the biological phenomena in which cancer cells lethally spread throughout the body. First, cancer cells detached from the primary site (e.g., epithelial tissue) breach the basement membrane separating them from other tissue layers. Some of these invasive cells can penetrate the basement membrane surrounding a blood vessel as well as the layer of endothelial cells lining it, which are then free to circulate via the bloodstream. Eventually, the cancer cells reach to a capillary, and adhere to and penetrate the capillary wall again, they can create a secondary tumor. Perhaps, fewer than one in 10,000 cancer cells that escape the primary site survives to form colony in another tissue (see: Erkki Ruoslahti, Scientific American, 72–77, September, 1996).

Therefore, tumor metastasis and invasion require adhesive interaction between cells and extracellular matrix ("ECM"). In the course of tumor metastasis, tumor cells can cause endothelial cells to retract, exposing the subendothelial basement membrane and allowing the tumor cells efficiently to adhere to ECM proteins of the surrounding stroma (see: Hynes, R. O., Cell, 48:549, 1987). These matrix proteins promote cell adhesion by binding to specific cell surface receptors, including a member of integrin family.

In terms of structure, each integrin is a heterodimer consisting of $\alpha$ and $\beta$ subunits which are noncovalently associated with each other. The $\beta1$ subfamily has been considered as a primary mediator of extracellular matrix adhesions. It has been reported that $\beta1$ integrins may have other functions, such as to mediate cell—cell adhesion directly (see: Larjava, H., et al., J. Cell. Biol., 110:803–815, 1990). The $\beta2$ subfamily that is found on leukocytes contains receptors mediating cell—cell interactions. The $\beta3$ subfamily includes the platelet glycoprotein IIb/IIIa complex and the vitronectin receptor, which may play an important role in the development of tumor invasiveness and malignancy (see: Albelda, S. M., et al., Cancer Res., 50:6757–6764, 1990).

The integrin receptor complex that is spanned the plasma membrane links the integral cytoskeletal network of a cell with the extracellular environment. Common or characteristic core sequences in cell adhesion molecules such as fibrinogen, vitronectin and laminin have been considered to contribute to cell adhesion and to the spread or integration of cells.

On the other hand, it was suggested that tumorigenesis and metastasis are closely associated with the biological role of integrins (see: Giancotti, F. G. and Rouslahti, E., Cell, 60:849–859, 1990; Hynes, R. O., Cell, 69:11–25, 1992; Nip, J., et al., J. Clin. Invest., 96:2096–2103, 1995).

Overexpression of fibronectin receptor $\alpha5\beta1$ suppressed the transformed phenotype of Chinese hamster ovary cells. Integrin $\alpha5\beta1$ was reduced in ras-transformed rodent cell (see: Plantefaben, L. C. and Hynes, R. O., Cell, 56:281–290, 1989) and superfibronectin that is a polymeric fibrillar form of fibronectin prevented tumor metastasis and tumor formation (see: Pasqualini, R., et al., Nature Medicine, 2:1197–1203, 1996).

Integrin $\alpha v\beta3$ is a specific marker of the most malignant cells, suggesting a crucial role of this adhesion receptor in the malignant growth of human melanoma (see: Albelda, S. M., et al., Cancer Res., 50:6757–6764, 1990). Integrin $\alpha v\beta3$ gene expression and the resulting adhesive phenotype are directly involved in the proliferation of human melanoma in vivo (see: Felding-Habermann, J. Clin. Invest., 89:2018–2022, 1992).

Angiogenesis is a biological process of forming new blood vessels as outgrowths from preexisting blood vessels (see: Folkman, J. and D'Amore, P. A., Cell, 87:1153–1155, 1996). This process plays a key role in the progression of solid tumor as well as normal development, wound healing and inflammation, and its regulation is contributed by vascular cell adhesion molecules in smooth muscle and endothelial cell (see: Nguyen, M., et al., Nature, 365:267, 1993).

The switch of angiogenic phenotype of tumor may be caused by losing balance between positive and negative modulators involved in neovascularization. Recently, it was reported that two cytokine-dependent pathways of angiogenesis were shown to exist and were defined by distinct vascular cell integrins, $\alpha v\beta3$ and $\alpha v\beta5$ that become expressed on angiogenic vascular cells where they play a critical role in angiogenesis induced by basic fibroblast growth factor ("bFGF"), tumor necrosis factor-alpha (TNF-$\alpha$), vascular endothelial growth factor (VEGF), and fragments of human tumors (see: Friedlander, M., et al., Science, 270:1500–502, 1995). Activation of $\alpha v\beta3$ integrin stimulates survival signal that facilitates blood vessel growth and differentiation indicating that signaling events by both cytokine and integrin receptors are closely associated with the growth of new blood vessels (see: Brooks, P. C., et al., Cell, 79:1157–1164, 1994).

On the other hand, several endogenous angiogenic inhibitors have been identified as followings: interferon-$\alpha$, -$\gamma$ (see: Friesel, R., et al., J. Cell. Biol., 104:689–696, 1987; Ezekowitz, R. A., et al., N. Engl. J. Med., 324:1456–1463, 1992); interferon-inducible protein 10(see: Angiolillo, A. L., et al., J. Exp. Med., 182:155–162, 1995; Strieter, R. M., et al., Biochem. Biophys. Res. Comm., 210:51–57, 1995); angiostatin and endostatin that specifically suppress endothelial cell proliferation (see: O'Reilly, M. S., et al., Cell, 79:315–328, 1994; O'Reilly, M. S., et al., Cell, 88:277–285, 1997); gro-$\beta$ (see: Cao, Y., et al., J. Exp. Med., 182:2069–2077, 1995); the 16 kDa N-terminal fragment of prolactin (see: Clapp, C., et al., Endocrinology, 133:1292–1299, 1993); and, platelet factor-4 (see: Maione, T., et al., Science, 247:77–79, 1990; Gupta, S. K., et al., Proc. Natl. Acad. Sci., USA, 92:7799–7803, 1995).

It has been well known that disintegrins are a family of small proteins mainly derived from snake venoms (see: Niewiarowski, S., et al., Semin. Hematol., 31:289–300, 1994). Most of the disintegrins contain Arg-Gly-Asp (RGD) or Lys-Gly-Asp (KGD) sequence which is the structural motif recognized by a platelet fibrinogen receptor $\alpha2b\beta3$, and also act as a potent antagonist of several integrins including $\alpha v\beta3$ and $\alpha5\beta1$. There are several reports demonstrating that disintegrins containing the RGD sequence inhibit tumor metastasis by blocking tumor cell adhesion to ECM (see: Trikha, M. et al., Cancer Res., 54(8):4993–4998, 1994).

Integrin αvβ3 was identified as a marker of angiogenic blood vessels in chick embryo and human (see: Brooks, P. C., et al., Science, 264:569–571, 1994). Monoclonal antibody against αvβ3 was able to perturb angiogenesis by inducing apoptosis in the endothelial cells of the newly formed blood vessels. Application of synthetic peptides containing the RGD sequence that inhibit ligand binding to integrin αvβ3 suppressed tumor-induced angiogenesis on chick chorioallantoic membrane ("CAM") (see: Brooks, P. C., et al., Cell, 99:1157–1164, 1994), and also suppressed the function of angiogenin which assists adhesion and diffusion of endothelial cells. Recently, triflavin, a disintegrin derived from snake venom, is reported to inhibit angiogenesis induced by TNF-α. These findings suggest that disintegrins, synthetic RGD peptides and anti-αvβ3 monoclonal antibody may be developed as a potent anti-tumor agent.

In line with the previous reports, the present inventors isolated Salmosin derived from venom of Korean snake, Agkistrodon halys brevicaudus, and characterized that: it is a novel protein of 7.5 kDa having a strong inhibitory activity against platelet agglutination (see: Korean Patent No. 142606, SEQ ID NO:1); and, it contains RGD sequence which is known to inhibit ligand binding to integrin αvβ3.

Under the circumstances, there are strong reasons for exploring and developing an anti-tumor agent comprising an active ingredient of Salmosin derived from venom of Agkistrodon halys brevicaudus.

SUMMARY OF THE INVENTION

The present inventors isolated and purified Salmosin from venom of Korean snake Agkistrodon halys brevicaudus, cloned cDNA thereof and overexpressed recombinant Salmosin in E. coli. Then, they have developed an anti-tumor agent comprising an active ingredient of Salmosin which is a disintegrin containing RGD sequence, based on the finding that Salmosin can strongly inhibit tumor angiogenesis which is essential to cancer cell growth and metastasis without affecting proliferation of normal endothelial cell.

A primary object of the present invention is, therefore, to provide an anti-tumor agent comprising an active ingredient of Salmosin derived from venom of Korean snake, Agkistrodon halys brevicaudus.

BRIEF DESCRIPTION OF DRAWINGS

The above and the other objects and features of the present invention will become apparent from the following description given in conjunction with the accompanying drawings, in which.

DETAILED DESCRIPTION OF THE INVENTION

The present inventors isolated and purified Salmosin from venom of Korean snake, Agkistrodon halys brevicaudus, screened cDNA thereof and overexpressed recombinant Salmosin in E. coli. They investigated the biological effect of both isolated and recombinant Salmosin on tumor metastasis and tumor growth in vivo and in vitro as well. As a result, they found that: Salmosin strongly inhibits the function of αvβ3 integrin which is crucial to tumor angiogenesis; and, it effectively suppresses metastasis and growth of tumors.

The present invention is further illustrated as follows.

Salmosin was isolated and purified from venom of Korean snake, Agkistrodon halys brevicaudus, using a series of column chromatographies and cloned cDNA thereof from the venom gland cDNA library of Agkistrodon halys brevicaudus. To investigate whether Salmosin may suppress metastasis of tumor cell, Salmosin was mixed with melanoma cells and injected into the lateral tail vein of mouse. Salmosin did not inhibit the proliferation of tumor cell itself in vitro, while it inhibited tumor cell angiogenesis in dose-dependent manner. These findings strongly suggested that the suppressive effect of Salmosin on tumor metastasis is grounded on inhibition of the function of integrin relating to tumor metastasis, not on its cytotoxicity. In this connection, the present inventors investigated whether Salmosin may inhibit the function of αvβ3 integrin which is associated with tumor angiogenesis through BCE cell proliferation test. As a result, it was found that: Salmosin inhibits tumor-induced angiogenesis without affecting the preexisting blood vessels or the angiogenesis; and, the suppressive effect of Salmosin on BCE cell proliferation results from the direct binding of Salmosin to vitronectin receptor, αvβ3 integrin, on BCE cell surface.

On the other hand, it was well known that disintegrin inhibits colony formation of metastatic tumor, but it was not clear whether disintegrin inhibits the growth of metastatic tumor already formed. Thus, to examine the effect of Salmosin on the growth of metastatic tumor, metastatic Lewis lung carcinoma cells were injected to the mouse and after the colony formation, Salmosin was injected. As a result, it was demonstrated that the metastatic tumor growth was effectively suppressed without any symptom of cytotoxicity and Salmosin also inhibited the growth of solid tumor.

The present invention is further illustrated in the following examples, which should not be taken to limit the scope of the invention.

EXAMPLE 1

Isolation of Salmosin from Venom

To purify Salmosin from venom of Korean snake, *Agkistrodon halys brevicaudus*, 1 ml of venom was suspended with 20 mM Tris•HCl-buffer (pH 7.5, "buffer A") to a volume of 10 ml, and applied into benzamidine-Sepharose (Pharmacia-LKB, Sweden) column which is equilibrated with buffer A, at a flow rate of 30 ml/hr. The unbound fractions of the column were collected and suspended with buffer A, and applied again into DEAE-Toyopearl column (2.5×5.0 cm) (Pharmacia-LKB, Sweden) at a flow rate of 60 ml/hr. The step elution was carried out at concentrations of 25 mM, 50 mM, 100 mM and 1M NaCl and the active fractions were concentrated with ultrafiltration system (Amicon, U.S.A.). The concentrated material was applied onto TSK-G2000 column (7.5×300 mm) (Toyosoda, Japan) and eluted with PBS (phosphate buffered saline). Active fractions were pooled, concentrated and applied onto reverse-phase Vydac C18 column (2.5×300 mm) (Vydac, U.S.A.) equilibrated with 0.1% TFA (trifluoroacetic acid) solution. And then, the column was alternately washed with the said TFA solution and 20% (v/v) acetonitrile solution and the protein was eluted with a linear gradient of 20–60% (v/v) acetonitrile in the said TFA solution.

EXAMPLE 2

Expression and Purification of Recombinant Salmosin

Figure 1:
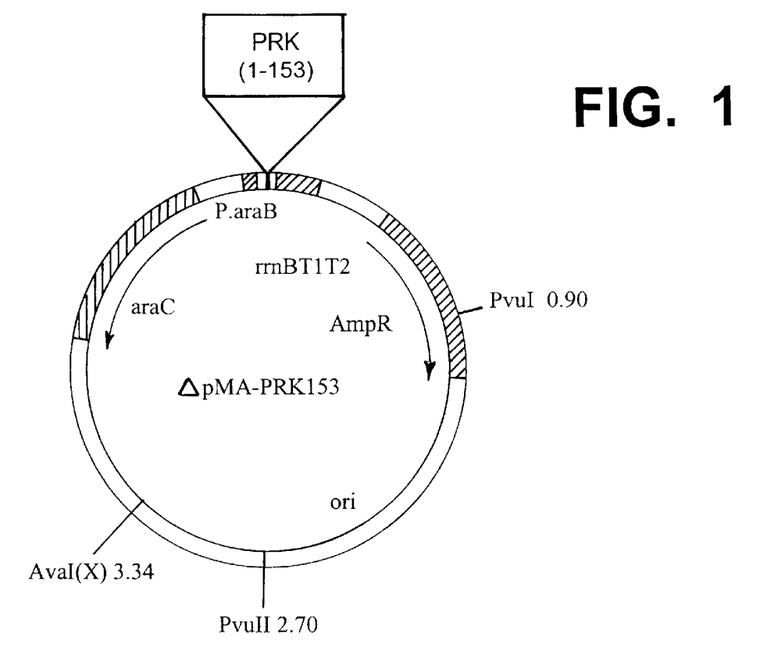
FIG. 1 is a genetic map of a recombinant expression vector ΔpMA-PRK153 encoding phosphoribulose kinase (PRK).
Figure 2A:
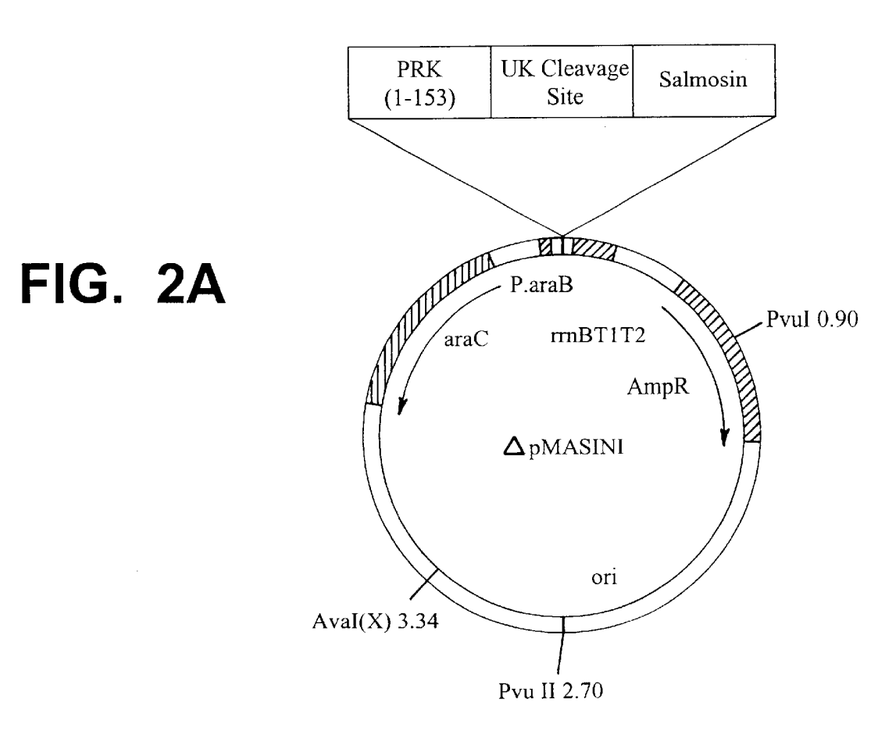
FIG. 2A is a genetic map of a recombinant expression vector ΔpMASIN1 encoding a fusion protein which consists of PRK153, urokinase cleavage site and Salmosin.

To clone cDNA encoding Salmosin, polymerase chain reaction (PCR) was performed with the venom gland cDNA library of *Agkistrodon halys brevicaudus* as a template. In carrying out PCR, oligo d(T) was employed as 3' primer and the nucleotide sequence (SEQ ID NO: 2) deduced from N-terminal amino acid sequence (-EECDCG- (SEQ ID NO: 5)) of Salmosin was employed as 5' primer. POR product of 290 bp was purified by agarose gel electrophoresis and cloned into a vector pCR II (Invitrogen, U.S.A.). The cloned DNA sequence was analyzed (SEQ ID NO: 3) and the amino acid sequence translated from the said DNA sequence was consistent with that of isolated Salmosin. For the expression of recombinant Salmosin, an *E.coli* expression vector, ΔpMA-PRK153 was employed (see: FIG. 1). In this vector, the protein of interest is expressed as a fusion protein to the phosphoribulose kinase (PRK) under the control of the araB promoter. For the facilitation of the subcloning, the DNA fragment generated by PCR was modified by introducing BamHI and XhoI site. Urokinase cleavage site was also introduced between the coding sequences of phosphoribulose kinase and Salmosin and an expression vector thus prepared was designated as ΔpMASIN1 (see: FIG. 2A). In FIG. 2A, P araB represents araB promoter, PRK(1–153) represents the protein comprising amino acid sequence from 1 to 153 and UK represents the cleavage site of urokinase.

The said expression vector was transformed in the *E.coli* strain MC1061. The transformants were grown in 1 L of 2×YT medium to an absorbance of 0.3 at a wavelength of 600 nm, induced with 1% arabinose (w/v) and incubated at 37° C. for 18 hr. Salmosin was expressed as an insoluble inclusion body and the inclusion body was resuspended in a pellet wash solution (0.5% Triton X-100, 1 mM EDTA, 1 mM DTT) and centrifuged at 12,000 rpm for 20 mm to remove contaminated *E.coli* proteins. After washing 3 more times, the pellet was solubilized in 20 ml of 8M urea solution (8M urea, 20 mM Tris•HCl, pH 7.8, 20 μM DTT) and incubated at 4° C. for 24 hr. After centrifugation, the clear supernatant was dialyzed against 4L of dialysis buffer (80 mM NaCl, 20 mM Tris•HCl, pH 7.8, 0.3% SDS) at 4° C. The refolded fusion protein was then cleaved with urokinase at a ratio of 400 mg of fusion protein and 1 U of urokinase at room temperature for 30 mm. 10 mg of cleaved protein was loaded onto DEAE-Toyopearl column equilibrated with 20 mM Tris•HCl (pH 8.0) buffer and eluted with the same buffer containing 50 mM NaCl. Active fractions were pooled, concentrated and applied onto TSK-G200 HPLC column (2.15×30 cm) and eluted with PBS. Subsequently, to remove the inappropriately cleaved Salmosin, active fractions were applied onto semi-preparative C18 HPLC column (1.0×20 cm) and eluted with a linear gradient of 20–40% (v/v) acetonitrile in 0.1% TFA solution.

EXAMPLE 3

Comparative Assay of Recombinant Salmosin and Isolated Salmosin

Figure 2B:
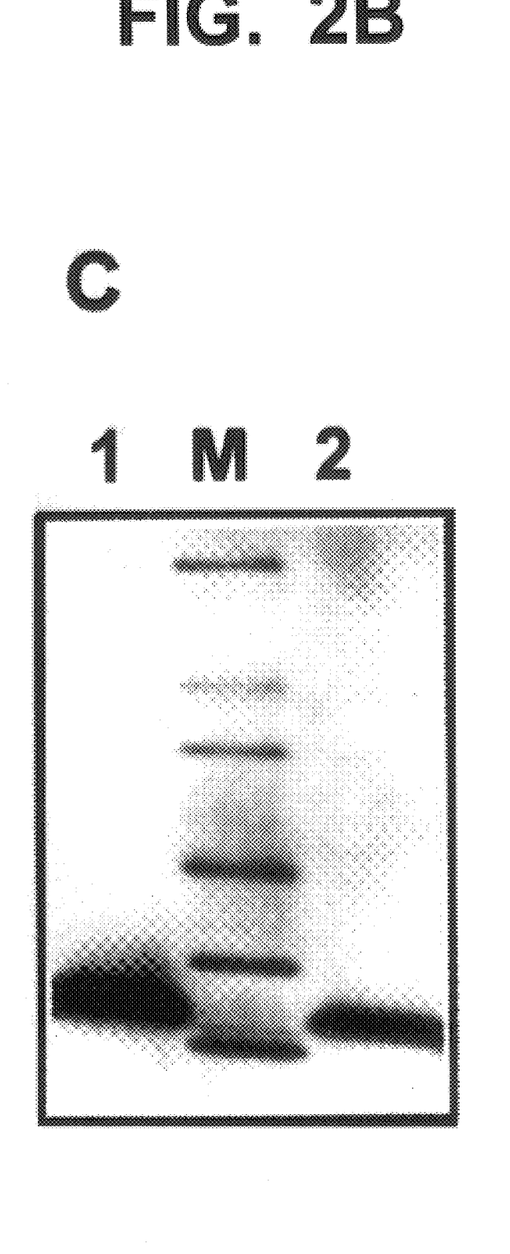
FIG. 2B is a photograph of SDS-PAGE pattern showing recombinant Salmosin and isolated Salmosin.
Figure 3A:
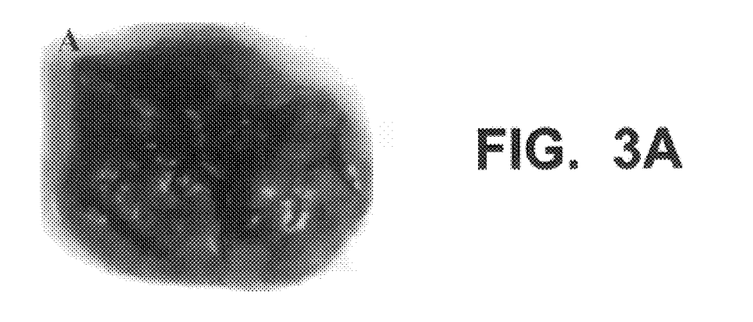
FIGS. 3A, B, C, and D show photographs of mouse lung in which B16 melanoma cell metastasis is suppressed by Salmosin.
Figure 3B:
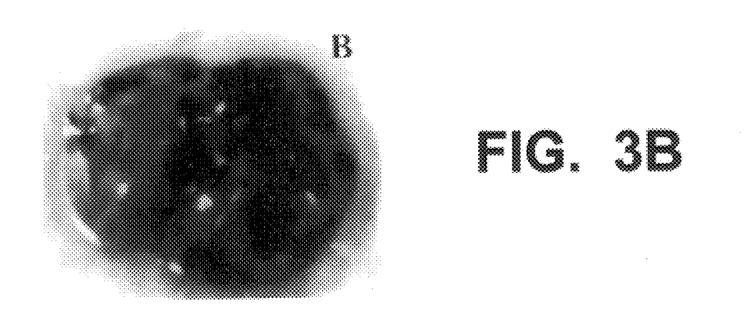
Figure 3C:
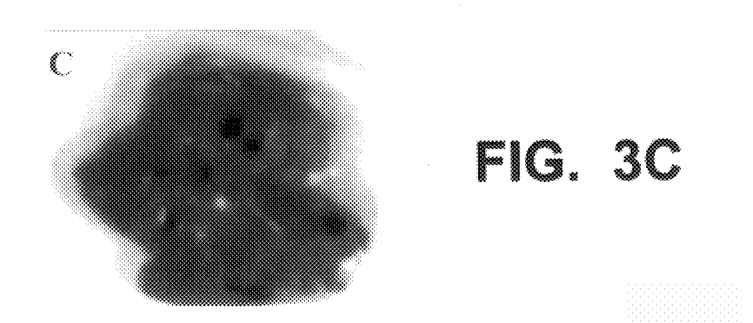
Figure 3D:
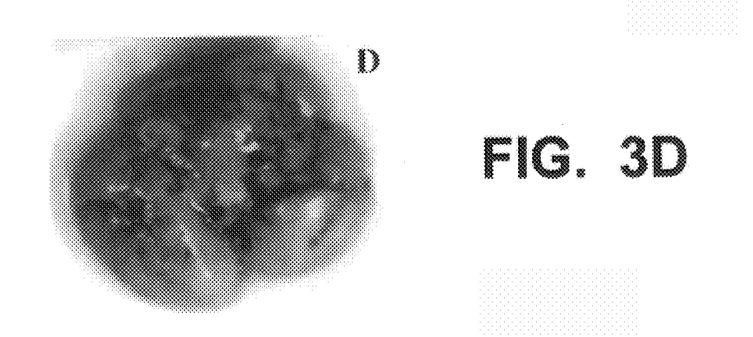

To compare physicochemical natures and biological activities of Salmosin prepared in Examples 1 and 2 described above, N-terminal sequencing, the platelet aggregation assay, and SDS-gel electrophoresis were carried out, respectively. The results showed that N-terminal sequence of recombinant Salmosin is initiated with the sequence of EAGEEC (SEQ ID NO: 6), which is consistent with that of isolated Salmosin and the suppressive activity of platelet aggregation is also identical. And, the result of SDS-PAGE indicated that the size of the recombinant Salmosin is exactly the same as that of the isolated salmosin (see: FIG. 2B). In FIG. 2B, lane 1 is the recombinant Salmosin, lane M is size marker, and lane 2 is the isolated Salmosin. Accordingly, it was clearly demonstrated that the recombinant Salmosin is correctly refolded and has the same biological activity as the isolated Salmosin.

EXAMPLE 4

Inhibition of Metastasis by Salmosin

To investigate the inhibitory effect of Salmosin on tumor metastasis in vivo, Salmosin was coinjected with B16 melanoma cells into C57BL/6 mouse (Charles river, Japan). B16 melanoma cells were detached with 0.02% EDTA and resuspended gently to $7.5 \times 10^5$/ml in RPMI-1640 medium without serum. Salmosin (250, 500, 1,250 μg/kg mouse) was then mixed with the cells to prepare single-cell suspension containing the indicated amount of Salmosin or PBS, and the single-cell suspension of 200 μl aliquots were injected into the lateral tail veins of mice. 14 days later, the mice were sacrificed and the number of lung melanoma colonies was counted by dissecting microscope. As a result, it was detected that metastatic colonies were dramatically reduced when compared with the PBS-treated control group in the lungs of C57BL/6 mice (see: Table 1). As shown in Table 1, the inhibition of colony formation by Salmosin was in dose-dependent manner; lower dose (250 μg/kg mouse) of Salmosin was able to inhibit the colony formation in the lung, but few colonies were detectable when salmosin was administered with higher dose. These findings are consistent with histochemical analysis (see: FIG. 3: A, normal lung; B, PBS treatment; C, 250 μg Salmosin/kg treatment; D, 1,250 μg Salmosin/kg treatment)

TABLE 1

Inhibition of metastasis by the treatment of Salmosin

| Salmosin (μg/kg mouse) | Number of mouse | Average number of lung tumor colony | Percentage of inhibition (%) |
| --- | --- | --- | --- |
| 0 | 8 | 144 ± 40 | 0 |
| 250 | 7 | 49 ± 22 | 66 |
| 500 | 7 | 3 ± 2 | 98 |
| 1,250 | 6 | 1 ± 1 | 99 |

Further, it was demonstrated that the inhibition of metastasis by Salmosin is not caused by cytotoxicity, based on the experimental fact that incubation of the B16 melanoma cells in vitro with Salmosin did not affect their subsequent proliferation rate.

These experimental evidences strongly suggested that Salmosin inhibits tumor metastasis by acting as an antagonist of integrin receptors on the surface of tumor cells, based on the suppressive effect of Salmosin on adhesion and invasion of B16 melanoma cell to ECM.

EXAMPLE 5

Inhibition of Angiogenesis by Salmosin

EXAMPLE 5-1

BCE (Bovine Capillary Endothelial) Cell Proliferation Assay

Figure 4A:
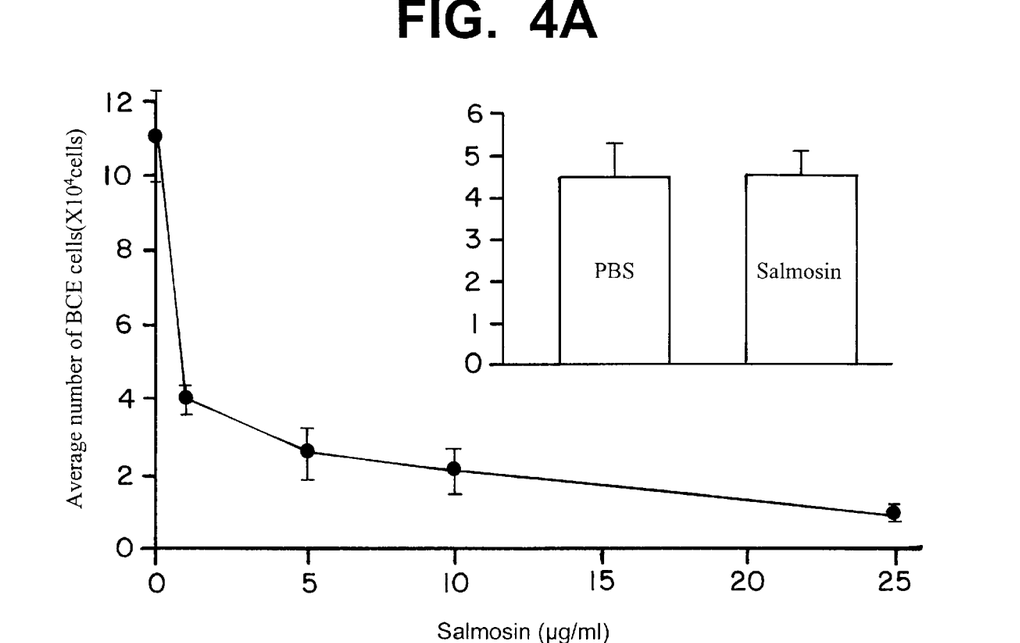
FIG. 4A is a graph showing the suppressive effect of Salmosin on proliferation of BCE (bovine capillary endothelial) cell stimulated by bFGF (basic fibroblast growth factor).
Figure 4B:
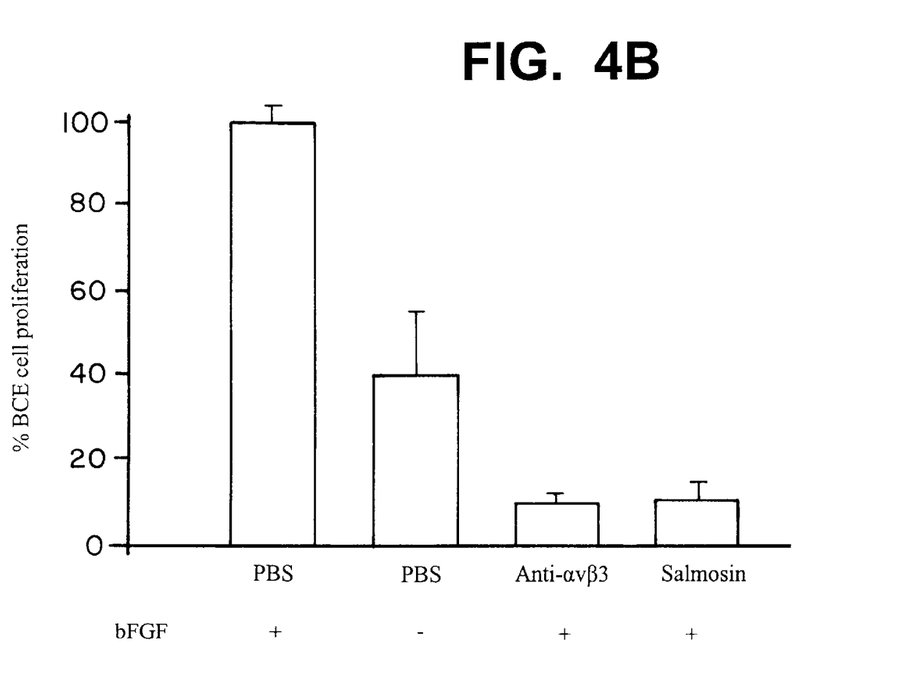
FIG. 4B is a graph showing the suppressive effect of anti-αvβ3 monoclonal antibody and Salmosin on proliferation of BCE cell stimulated by bFGF.

The suppressive effect of Salmosin on angiogensis was examined by employing BCE cell proliferation assay system. Primary culture of BCE cell from bovine adrenal was prepared, and then the cells were maintained in Dulbeco's minimum essential medium ("DMEM") containing 3 ng/ml of bFGF supplemented with 10% fetal calf serum. The said BCE cells were plated onto gelatinized 24-well culture plates and incubated at 37° C., 5% $CO_2$ for 24 hr. After incubation, the medium was replaced with DMEM containing 5% fetal calf serum, and Salmosin was added to the medium. After 20 min of incubation, bFGF (1 ng/ml) dissolved in the said medium was treated to the cells and after 72 hr, cells were detached with trypsin and the number of cells was counted. As a result, it was found that Salmosin is able to inhibit the proliferation of BCE cells stimulated by bFGF in a dose-dependent manner. Half-maximal inhibition was observed with Salmosin concentration of 0.1–0.2 μg/ml corresponding to 13–27 nM (see: FIG. 4A). In addition, the bFGF-stimulated BCE cells undergo remarkable morphological change into spherical shape by the treatment of Salmosin. However, it was observed that the cell proliferation is not inhibited in the absence of bFGF when the cells were treated with 20 μg/ml Salmosin which was required for maximal inhibition of bFGF-induced proliferation (see: graph in box of FIG. 4A). On the other hand, it was examined that anti-αvβ3 monoclonal antibody effectively inhibits bFGF-stimulated proliferation of BCE cells (see: FIG. 4B).

EXAMPLE 5-2

CAM (Chick Chorioallantoic Membrane) Assay

Figure 5A:
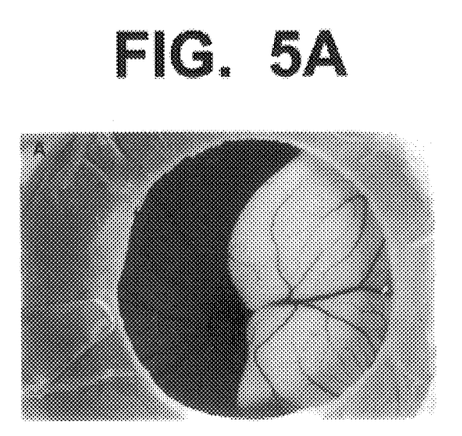
FIG. 5A is a photograph showing CAM (chick chorioallantoic membrane) angiogenesis induced by bFGF.
Figure 5B:
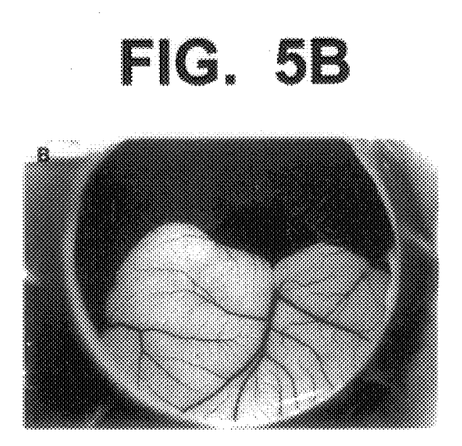
FIG. 5B is a photograph showing the suppressive effect of anti-αvβ3 monoclonal antibody on CAM angiogenesis induced by bFGF.
Figure 5C:
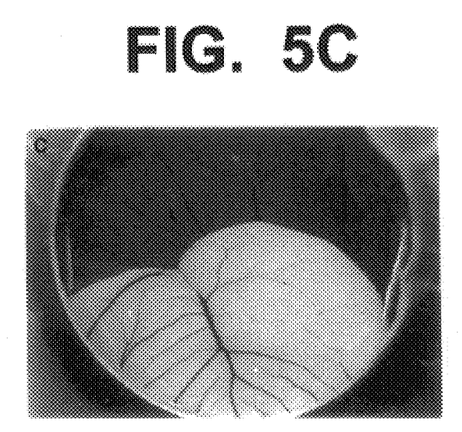
FIG. 5C is a photograph showing the suppressive effect of Salmosin on CAM angiogenesis induced by bFGF.

The suppressive effect of Salmosin on tumor-induced angiogenesis in vivo, was examined by CAM (chick chorioallantoic membrane) assay: Three-day-old fertilized eggs were carefully cracked and sealed with transparent tapes. For 10 days of incubation at 37° C. with 60% humidity, the said fertilized eggs were developed into embryo. After that, 6 ng of bFGF was implanted on the CAM of individual embryo to induce neovascularization. After 24 hr of incubation, 5 μg of Salmosin, 5 μg of anti-αvβ3 moniclonal antibody (positive control) or PBS (phosphate buffered saline, negative control) was treated on the CAM of individual embryo. And after 72 hr, blood vessels on CAM were observed under the stereomicroscope (see: FIGS. 5A, 5B and 5C). It was observed that: there was no visible change in the neovascularization when PBS was treated (see: FIG. 5A), while it was inhibited when Salmosin or anti-αvβ3 moniclonal antibody was treated (see: FIGS. 5B and 5C). Especially, it was found that Salmosin breaks new blood vessels which are induced by bFGF, indicating that Salmosin inhibits tumor-induced angiogenesis, without affecting the preexisting blood vessels or the angiogenesis that is a normal physiological phenomenon.

EXAMPLE 6

Inhibition of BCE Cell Adhesion by Salmosin

Figure 6A:
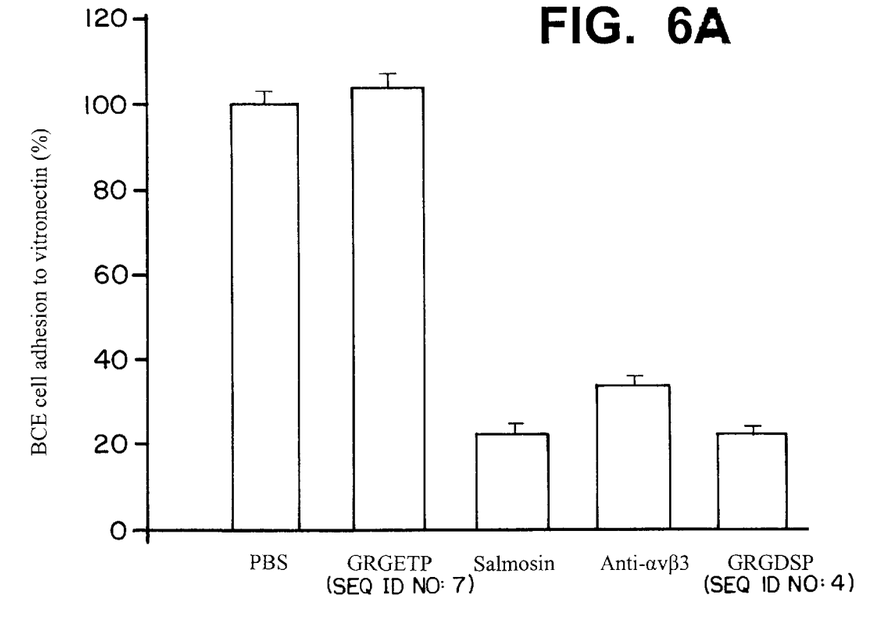
FIG. 6A is a graph showing the suppressive effect of Salmosin or other antagonists against αvβ3 integrin (i.e., anti-αvβ3 antibody or GRGDSP (SEQ ID NO: 4)) of adhesion vitronectin and BCE cell.
Figure 6B:
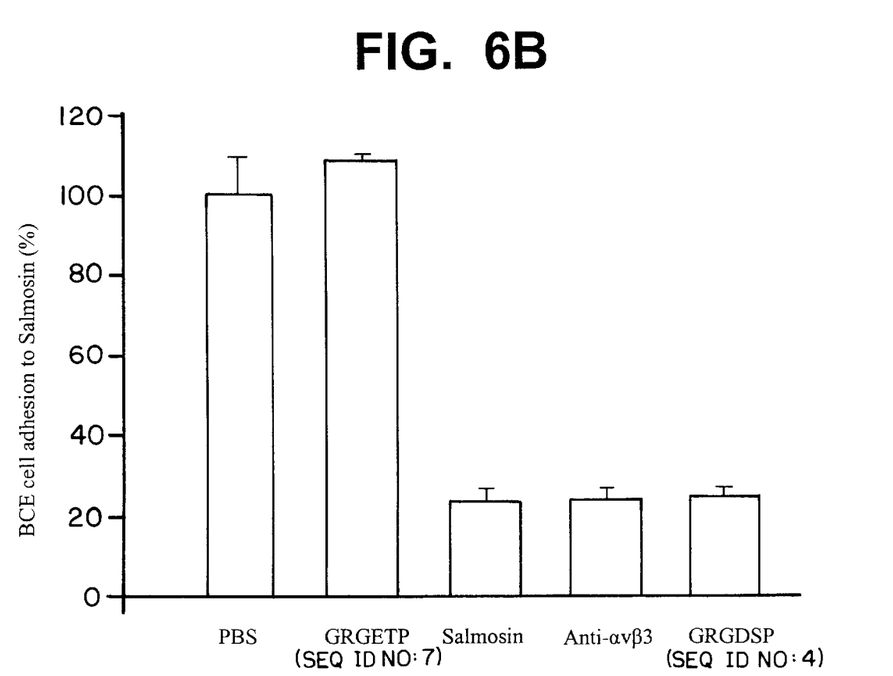
FIG. 6B is a graph showing the suppressive effect of Salmosin or other antagonists against αvβ3 integrin (i.e., anti-αvβ3 antibody or GRGDSP (SEQ ID NO: 4)) on adhesion of Salmosin and BCE cell.

To investigate whether the BCE cell proliferation is inhibited by direct-binding of Salmosin to αvβ3 integrin which is a vitronectin receptor on the surface of BCE cell, the capability of Salmosin which inhibits BCE cell adhesion to vetronectin was examined: 96-well microplates were coated with Salmosin (1 μg/well) and vitronectin (0.5 μg/well) in PBS at 4° C. for 16 hr. The said microplates were washed and incubated for 1 hr with 10 mg/ml of heat-denatured bovine serum albumin to block remaining protein binding sites, and washed with PBS before use. BCE cells were detached with trypsin-EDTA, washed three times in PBS, and resuspended in serum-free DMEM. $5 \times 10^4$ of cells were preincubated with Salmosin, anti-αvβ3 monoclonal antibody, synthetic RGD peptide (GRGDSP (SEQ ID NO: 4)) or synthetic RGE peptide (GRGETP (SEQ ID NO: 7)) for 20 mm and aliquoted to each well of the said plate, then further incubated at 37° C. for 1 hr in 5% $CO_2$, 95% air. Unbound cells were removed by washing with PBS, then the cells which bound to the plate were fixed and stained with Coomassie Blue. Absorbance at 540 nm of the individual well was measured to determine the relative cell number. As a result, it was found that: adhesion of BCE cell to vitronectin can be highly suppressed by preincubating the bEGE-stimulated cells with Salmosin (see: FIG. 6A); anti-αvβ3 monoclonal antibody strongly inhibits the cell adhesion to Salmosin (see: FIG. 6B); and, synthetic RGD peptide (GRGDSP (SEQ ID NO: 4)) is also able to prevent the cells from adhering to either vitronectin or Salmosin (see: FIGS. 6A and 6B). These results clearly demonstrated that Salmosin binds to βvβ3 integrin on BCE cells and thereby blocks the integrin-mediated cell adhesion.

EXAMPLE 7

Inhibition of Metastatic Tumor Growth by Salmosin

It has been reported that disintegrins suppress the colony formation of lung tumor by inhibiting the attachment of tumor cells to endothelium. However, it is not clear whether the disintegrins inhibit the growth of lung metastatic tumor or not. To investigate the suppressive effect of Salmosin on metastatic tumor growth, $1.5 \times 10^5$ of Lewis lung carcinoma cells obtained from ATCC (Rockville, U.S.A.) were injected into the lateral tail veins of 8-week-old male C57BL/6 mice, and metastatic colonies were developed in mice. 4 days later, Salmosin was administered intravenously to the mice once a day with a dose of 1.25 mg/kg/day; 4 weeks later, mice were sacrificed and lungs were removed; the number of lung tumor colony was counted under the dissecting microscope. and there was no recognizable symptom of toxicity in any mouse tested. As a result, it was demostrated that Salmosin remarkably inhibits the metastatic tumor growth (see: Table 2). In this regard, the suppressive effect of Salmosin on the metastatic tumor growth could be explained by binding of Salmosin to αvβ3 integrin which is essential for tumor angiogenesis.

TABLE 2

Growth inhibition of pulmonary metastatic Lewis lung carcinoma by Salmosin treatment

| Salmosin (mg/kg mouse) | Number of mouse | Average number of lung tumor colony | Inhibition (%) |
|---|---|---|---|
| 0 | 4 | 15 ± 6 | 0 |
| 4 | 4 | 0.8 ± 0.7 | 93 |

Figure 7A:
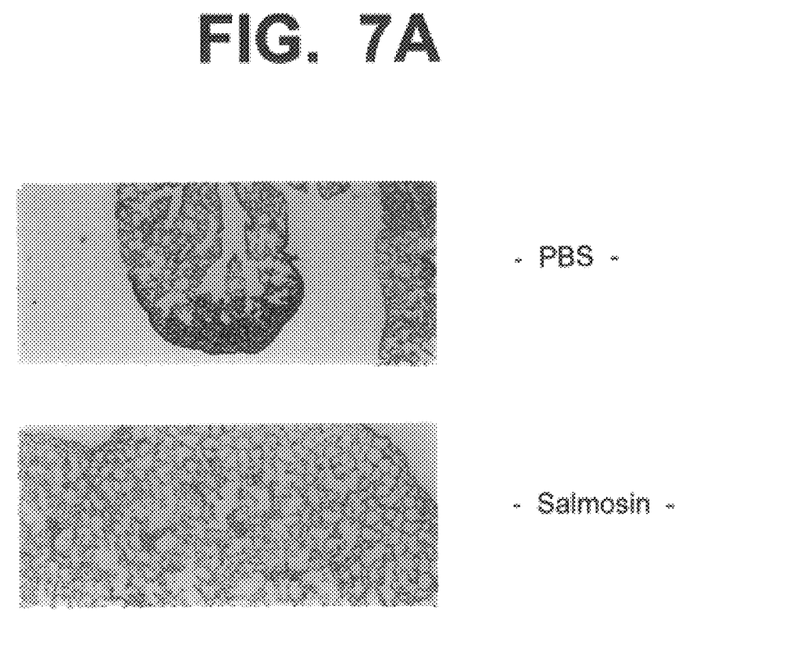
FIGS. 7A and B show photographs of mouse lungs showing the suppressive effect of Salmosin on growth of metastasis Lewis lung carcinoma (top: PBS treatment, bottom: Salmosin treatment).
Figure 7B:
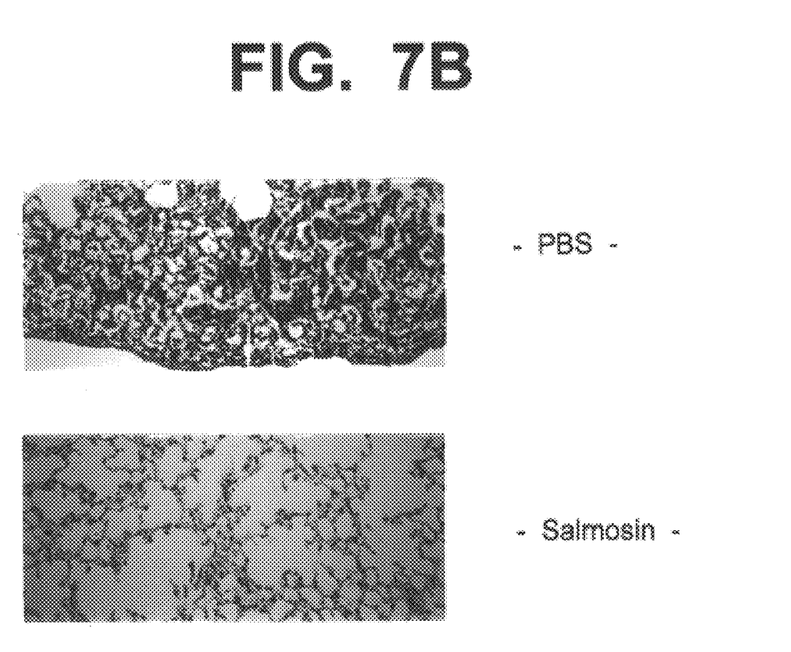

Further, histochemical analysis was carried out to investigate a suppressive effect of Salmosin on the pulmonary metastatic tumor. The said lung tissue was fixed for 4 hr in Bouin's soution and embedded in paraffin in accordance with the standard procedure. Sections of 4 μm thick were permeabilized with trypsin at 37° for 10 mm and washed with PBS. The said sections were stained with hematoxylin and eosin, and then mounted. It was observed that few of tumor colonies were detected in the lungs of Salmosin-treated animal (see: FIGS. 7A and B), which is quite different from those of PBS-treated control mice. FIG. 7 shows photographs of ×400 magnification (A) and ×200 magnification (B), respectively, suggesting that the suppressive effect of Salmosin on metastatic tumor growth is closely related to the suppression of angiogenesis which is necessary for secondary tumor growth.

EXAMPLE 8

Inhibition of Solid Tumor Growth by Salmosin

Figure 8:
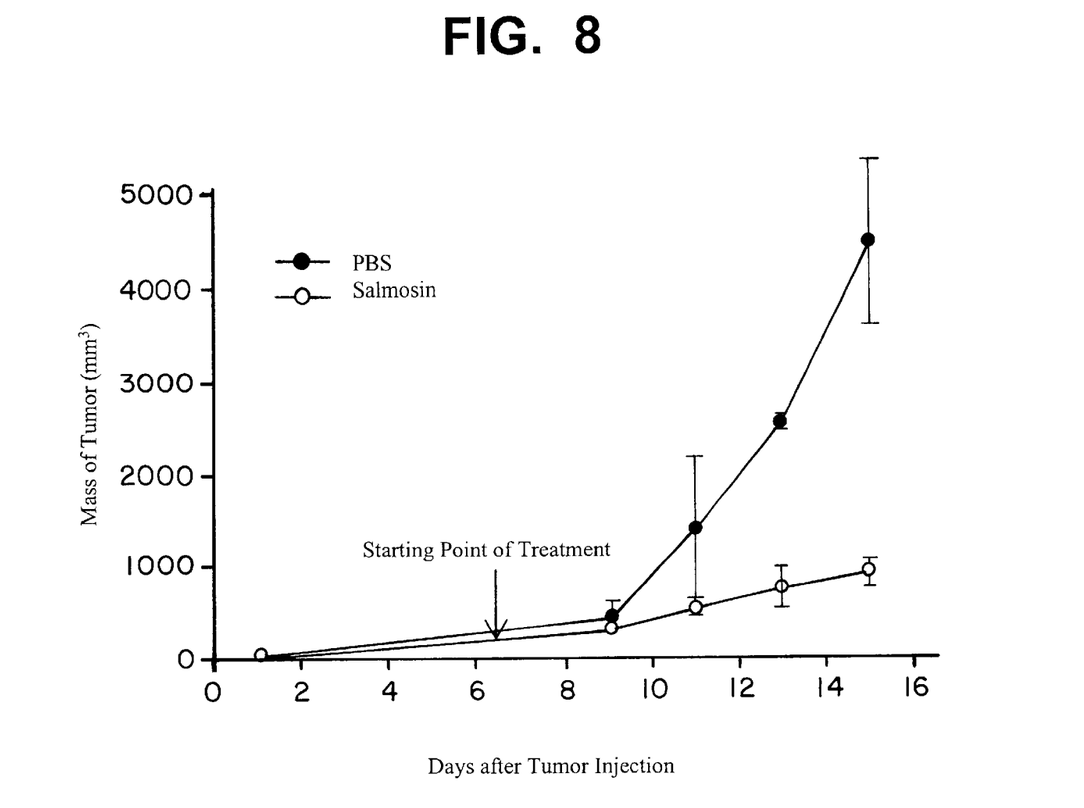
FIG. 8 is a graph showing the suppressive effect of Salmosin on growth of solid Lewis lung carcinoma.

To examine the role of Salmosin in the growth of solid tumor, Lewis lung carcinoma cells ($1 \times 10^6$) were injected subcutaneously into dorsal midline of C57BL/6 mice and grown to a mass of at least 100–200 mm$^3$. After the mice were randomized into two groups, one group received injections of Salmosin (10 mg/kg mouse) in PBS via subcutaneous injection at a site distant from the tumor once daily and the other group as a control received injections of PBS alone. The size of the tumors in all groups were measured at the same time everyday and the experiments were terminated when the control mice began to die. As a result, it was observed that the growth of solid tumor is strongly inhibited by the treatment of Samosin (see: FIG. 8)

Administration and Effective Dose

Though the effective dose of Salmosin is variable depending on age, body weight of patient and progression of disease, it is preferable to administer parenterally 0.5 to 10 mg/kg/day in a single dose, and which may be individualized by experience of the skilled in the art.

Acute Toxicity Test

To examine the acute toxicity of Salmosin, Salmosin was injected into male C57BL/6 mouse subcutaneously and the deads were counted to determine $LD_{50}$ for 7 days. As a result, $LD_{50}$ is determined as about 1,000 mg/kg, indicating that the anti-tumor agent comprising Salmosin is sufficiently safe within the range of effective dose.

The pharmaceutical composition of the present invention which comprises an active ingredient of Salmosin and pharmaceutically acceptable carrier may be administrated as an injection formula. The injection formula may further comprise isotonic aqueous solution or suspension, and the pharmaceutically acceptable carrier covers preservatives, stabilizers, wetting agents, emulsifiers, salts for changing osmotic pressure or buffers.

While the present invention has been shown and described with reference to the particular embodiments employing melanoma cells and Lewis lung carcinoma cells as tested tumor cells, the anti-tumor agent of the invention may be effective for various tumors such as skin cancer, laryngeal cancer, uterine cancer, colon cancer, lung cancer and bone marrow cancer.

As clearly illustrated and demonstrated as above, the present invention provides an anti-tumor agent comprising an active ingredient of Samosin. In accordance with the present invention, it was demonstrated that Salmosin is a novel disintegrin which blocks the function of αvβ3 integrin and strongly inhibits tumor angiogenesis, tumor metastasis as well as growth of solid tumor. Salmosin does not exhibit cytotoxicity within an effective dose range where tumor growth is efficiently suppressed without any untoward effect on preexisting blood vessels and normal angiogenesis. Accordingly, Salmosin can be applied for the development of potent anti-tumor drugs which are effective for various types of cancers.

What is claimed is:

1. A method of treating cancer, comprising administering a composition comprising a pharmaceutically effective amount of Salmosin derived from venom of *Agkistrodon halys brevicaudus,* the Salmosin comprising the amino acid sequence SEQ ID NO:1, and one or more pharmaceutically acceptable carriers.

2. The method of claim 1, wherein said cancer comprises skin cancer, laryngeal cancer, uterine cancer, colon cancer, lung cancer and bone marrow cancer.

* * * * *